(12) United States Patent
Keltjens et al.

(10) Patent No.: US 10,471,156 B2
(45) Date of Patent: Nov. 12, 2019

(54) PHARMACEUTICAL COMPOSITION COMPRISING AMORPHOUS LENALIDOMIDE

(71) Applicant: SYNTHON B.V., Nijmegen (NL)

(72) Inventors: Rolf Keltjens, Nijmegen (NL); Jacobus Theodorus Henricus Van Eupen, Nijmegen (NL); Deepak Murpani, Nijmegen (NL); Marta Vivancos Martinez, Sant Boi de Llobregat (ES); Lisardo Alvarez Fernandez, Sant Boi de Llobregat (ES); Luis Nogueiras Nieto, Sant Boi de Llobregat (ES)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 15/537,833

(22) PCT Filed: Dec. 16, 2015

(86) PCT No.: PCT/EP2015/080054
§ 371 (c)(1),
(2) Date: Jun. 19, 2017

(87) PCT Pub. No.: WO2016/097025
PCT Pub. Date: Jun. 23, 2016

(65) Prior Publication Data
US 2017/0368197 A1    Dec. 28, 2017

(30) Foreign Application Priority Data

Dec. 19, 2014   (WO) ................ PCT/EP2014/078791

(51) Int. Cl.
| | | |
|---|---|---|
| *A61K 47/69* | (2017.01) | |
| *A61K 31/454* | (2006.01) | |
| *A61K 9/48* | (2006.01) | |
| *C08B 37/16* | (2006.01) | |

(52) U.S. Cl.
CPC ........ *A61K 47/6951* (2017.08); *A61K 9/4858* (2013.01); *A61K 9/4866* (2013.01); *A61K 31/454* (2013.01); *C08B 37/0015* (2013.01)

(58) Field of Classification Search
None
See application file for complete search history.

(56) References Cited

U.S. PATENT DOCUMENTS

2012/0046315 A1   2/2012  Rimkus et al.

FOREIGN PATENT DOCUMENTS

| CN | 103610658 | 3/2014 |
|---|---|---|
| CN | 103705485 | 4/2014 |
| EP | 925294 B1 | 12/2002 |
| WO | WO2005023192 | 3/2005 |
| WO | WO 2009114601 | 9/2009 |
| WO | WO2010054833 | 5/2010 |
| WO | WO2011111053 | 9/2011 |

OTHER PUBLICATIONS

Machine translation of Specification of CN103705485 A, 27 pages, machine translation obtained on Dec. 8, 2018 from European Patent Office website.*
Remington: The Science and Practice of Pharmacy, 21st Edition, 2005, pp. 1054-1055.*
(Arthur H. Kibbe (Ed.), Handbook of Pharmaceutical Excipients, Third Edition 2000, p. 165-168).
Thorstein Loftsson at al., Pharmaceutical Sciences, 85(10), 1996, 1017-1025.
John L. Koontz et al., J. Agric. Food Chem., 57(4), 2009, p. 1162-1171.
József Szejtli (Cyclodextrin Technology, 1986, p. 81.

* cited by examiner

*Primary Examiner* — Savitha M Rao
*Assistant Examiner* — Gregg Polansky
(74) *Attorney, Agent, or Firm* — Buscher Patent PLLC

(57) ABSTRACT

The present invention relates to a pharmaceutical composition comprising an inclusion complex of amorphous lenalidomide, or a pharmaceutically acceptable salt thereof, in non-substituted β-cyclodextrin and one or more pharmaceutically acceptable excipients. The invention further relates to the use of said composition as a medicament, particularly in the treatment of in the treatment of multiple myeloma and myelodysplastic syndromes.

12 Claims, No Drawings

PHARMACEUTICAL COMPOSITION COMPRISING AMORPHOUS LENALIDOMIDE

BACKGROUND OF THE PRESENT INVENTION

Lenalidomide, chemically (RS)-3-(4-Amino-1-oxo 1,3-dihydro-2H-isoindol-2-yl)piperidine-2,6-dione of formula (I),

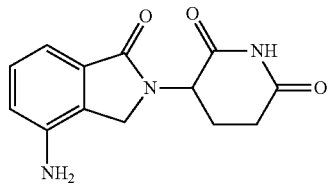 [SMILES: Nc1cccc2c1CN(C1CCC(=O)NC1=O)C2=O]

is a pharmaceutically active compound used for the treatment of multiple myeloma and Myelodysplastic syndromes The compound was discovered by Celgene and is disclosed in EP925294. Lenalidomide is the active ingredient in the medicinal product sold under the brand name Revlimid®.

Lenalidomide exhibits polymorphism. WO2005023192 discloses crystalline forms of lenalidomide, its process of preparation, compositions comprising these crystalline forms and its use for treatment of diseases. Polymorph B is the most stable form and is present in the marketed tablets. Compositions comprising both amorphous and crystalline lenalidomide are also disclosed in this application. Other polymorphic forms of lenalidomide are disclosed in WO2011111053. The prior art thus teaches that lenalidomide crystallizes very easily. Moreover, it was experienced in our laboratory that polymorphic transitions of lenalidomide take place rather easily, especially in drug product.

Lenalidomide is slightly soluble in water. Conventional approaches to increase solubility consist on micronizing the API. Nevertheless, it was experienced in our laboratory that micronization of lenalidomide gave partially amorphous solid, which readily converts to other crystalline forms. It is known that generally the solubility of amorphous forms is higher compared to the solubility of crystalline forms. In view of this, it would be desirable to produce stable amorphous lenalidomide and to find a robust process for making such a stable amorphous lenalidomide.

WO2010054833 and WO 2009114601 disclose solid dispersions containing amorphous lenalidomide.

Although many drugs can be solubilized by cyclodextrin it is not apparent that the inclusion complex obtained is completely amorphous.

CN103705485 discloses the use of beta cyclodextrines as solubilising agent in lenalidomide formulations in a ratio of 1:8. It was experienced in our laboratory that in this ratio the inclusion complex obtained is partially amorphous and therefore not stable.

Thus in view of the prior art cited above, there is still a need for alternative pharmaceutical compositions comprising lenalidomide, or a pharmaceutically acceptable salt thereof, which are stable and suitable for use on a commercial scale.

BRIEF DESCRIPTION OF THE PRESENT INVENTION

The present invention relates to a pharmaceutical composition comprising an inclusion complex of amorphous lenalidomide, or a pharmaceutically acceptable salt thereof, with a non-substituted β-cyclodextrin and one or more pharmaceutically acceptable excipients, in a weight ratio of lenalidomide to non-substituted β-cyclodextrin ranges from 1:1 to 1:4, exhibiting a dissolution rate of at least 85% in 15 minutes when tested in 900 ml SGF pH 1.2, pH 2 acetate buffer pH 4.5 or phosphate buffer pH 6.8 in a USP apparatus II at 75 rpm in standard vessels or 50 rpm with peak vessels.

It also provides a process for preparing said inclusion complex comprising dissolving lenalidomide, or a pharmaceutically acceptable salt thereof, in a suitable solvent or solvent mixture and mixing with non-substituted β-cyclodextrin, followed by evaporation of the solvent(s).

Additionally, the invention provides a process for preparing said pharmaceutical composition comprising mixing or granulating said inclusion complex with one or more excipients, followed by encapsulation.

Said pharmaceutical composition may be used as a medicament, particularly in the treatment of multiple myeloma and myelodysplastic syndromes.

DETAILED DESCRIPTION OF THE PRESENT INVENTION

The present invention relates to a pharmaceutical composition comprising an inclusion complex of amorphous lenalidomide, or a pharmaceutically acceptable salt thereof, with a non-substituted β-cyclodextrin and one or more pharmaceutically acceptable excipients, in a weight ratio of lenalidomide to non-substituted β-cyclodextrin ranges from 1:1 to 1:4, exhibiting a dissolution rate of at least 85% in 15 minutes when tested in 900 ml SGF pH 1.2, pH 2 acetate buffer pH 4.5 or phosphate buffer pH 6.8 in a USP apparatus II at 75 rpm in standard vessels or 50 rpm with peak vessels.

Cyclodextrins are compounds made up of sugar molecules bound together in a ring and are composed of 5 or more α-D-glucopyranoside units linked 1→4. Cyclodextrins are produced from starch by means of enzymatic conversion. Three major non-substituted cyclodextrins are known, containing each a different number of glucose monomers ranging from six to eight in a ring, creating a conical shape. The so-called α-cyclodextrin is a six-membered sugar ring molecule, β-cyclodextrin is a seven-membered sugar ring molecule and γ-cyclodextrin is an eight-membered sugar ring molecule.

Cyclodextrins may form complexes with various chemicals (guest molecules), in which the chemical is encapsulated inside the cyclodextrin ring and forms a so called inclusion complex. Thereby, original properties of the compound vis-à-vis the cyclodextrin-complexed compound may be modified (Arthur H. Kibbe (Ed.), Handbook of Pharmaceutical Excipients, Third Edition 2000, p. 165-168).

Drugs that can exist in either amorphous or crystalline form tend to crystallize over time when present in amorphous state because the crystalline form of the drug is a lower-energy state than the amorphous form. Active Pharmaceutical Ingredients (APIs) may form inclusion complexes in cyclodextrins wherein the API in the inclusion complex is kept in amorphous form (Thorstein Loftsson at al., Pharmaceutical Sciences, 85(10), 1996, 1017-1025). It is however not self-evident that a given drug will form an inclusion complex with just any cyclodextrin, and that, even in the event the complex is formed, it will be stable over time. Factors playing a role herein are the physicochemical properties of both API and cyclodextrin, the ratio of API to cyclodextrin used and the technique used to prepare the complex. Although cyclodextrin complexation procedures are relatively simple processes, these techniques often require very specific conditions for each guest molecule (John L. Koontz et al., J. Agric. Food Chem., 57(4), 2009, p. 1162-1171).

CN103705485 suggests that lenalidomide can be solubilized by beta cyclodextrin and its derivatives. Unlike α, γ, and β substituted cyclodextrin, non-substituted β-cyclodextrin exhibits low aqueous solubility. 2-hydroxypropyl-β-cyclodextrin, which is a partially substituted poly(2-hydroxypropyl)ether of β-cyclodextrin has a high aqueous solubility exceeding 600 mg/ml while non-substituted β-cyclodextrin has a solubility of 18.5 mg/ml.

Surprisingly, the present inventor has discovered lenalidomide, or a pharmaceutically acceptable salt thereof, in a specific weight ratio to non-substituted β-cyclodextrin of 1:1 to 1:4, yields to more stable inclusion complexes with amorphous lenalidomide, or a pharmaceutically salt thereof. During stability studies no conversion into any crystalline form was observed even under stress conditions. Experimental results suggest that ratios higher than 1:5 result in partially crystalline complexes which are not stable.

The weight ratio of lenalidomide, or a pharmaceutically acceptable salt thereof, to non-substituted β-cyclodextrin in the inclusion complex ranges from about 1:1 to about 1:4 and is preferably 1:1 or 1:2.

It is surprising that the excellent stability of the inclusion complex of the current invention is present at such low weight ratios of lenalidomide, or a pharmaceutically acceptable salt thereof, to non-substituted β-cyclodextrin. During stability studies no conversion into any crystalline form was observed, even under stress conditions. With regard to impurity levels, also no significant differences have been observed, showing sufficient long term stability.

At a weight ratio 1:1 to 1:4 the stability of the amorphous lenalidomide in the inclusion complex of the present invention can not only be explained for by (partial) encapsulation of lenalidomide, in the cyclodextrin cavity. Lenalidomide is also accommodated in the intermolecular cavities formed or sandwich-like between layers of non-substituted β-cyclodextrin. As described by József Szejtli (Cyclodextrin Technology, 1988, p. 81), the "intercalation" enhances the molar ratio in favor of the guest molecule, which could account for that, although lenalidomide or a pharmaceutically acceptable salt thereof, is present in excess amounts over the non-substituted β-cyclodextrin, the stability of the pharmaceutical compositions is still excellent. It is however not evident that lenalidomide might form stable compositions in the same way with substituted cyclodextrins.

The pharmaceutical compositions prepared with the inclusion complex display dissolution behavior typical for immediate-release formulations. The compositions of the present invention exhibit a dissolution rate of at least 85% in 15 minutes when tested in 900 ml SGF pH 1.2, pH 2, acetate buffer pH 4.5 or phosphate buffer pH 6.8 in a USP apparatus II at 75 rpm in standard vessels or 50 rpm with peak vessels.

At least a major portion of lenalidomide, or a pharmaceutically acceptable salt thereof, in the inclusion complex is amorphous. The term "a major portion" of lenalidomide, or a pharmaceutically acceptable salt thereof, means that at least 60% of the drug is in amorphous form, rather than a crystalline form. Preferably, lenalidomide, or a pharmaceutically acceptable salt thereof, in the inclusion complex is at least 80% in amorphous form. More preferably, lenalidomide, or a pharmaceutically acceptable salt thereof, in the inclusion complex is "almost completely amorphous" meaning that the amount of lenalidomide, or a pharmaceutically acceptable salt thereof, in the amorphous form is at least 90% as measured by powder X-ray diffraction or any other standard quantitative measurement. Most preferably, lenalidomide, or a pharmaceutically acceptable salt thereof, in the inclusion complex is in a completely amorphous form within the detection limits of the techniques used for characterization.

The pharmaceutical compositions of the present invention comprise the inclusion complex of lenalidomide, or a pharmaceutically acceptable salt thereof, in non-substituted β-cyclodextrin and one or more pharmaceutically acceptable excipients, wherein the weight ratio of lenalidomide to non-substituted β-cyclodextrin ranges from 1:1 to 1:4. The excipients to be used in accordance with the present invention are well-known and are those excipients which are conventionally used by the person skilled in the art. Depending on the dosage form chosen for the pharmaceutical composition, the person skilled in the art will be able to select suitable pharmaceutically acceptable excipients. Preferably, the dosage form is an immediate release capsule and the pharmaceutically acceptable excipients are chosen from one or more binders, diluents, disintegrants, glidants, lubricants, stabilizers, surface active agents or pH-adjusting agents. More preferably, the composition of the present invention comprises a diluent, a disintegrant and a lubricant.

The diluent to be used in accordance with the present invention may be any diluent known to a person of ordinary skill in the art. Particularly, the diluent to be used in accordance with the present invention is an inorganic diluent, polysaccharide, mono- or disaccharide or sugar alcohol. Microcrystalline cellulose is a particularly preferred diluent.

The disintegrant to be used in accordance with the present invention may be any disintegrant known to a person of ordinary skill in the art. Suitable disintegrants to be used in accordance with the present invention are selected from the group consisting of croscarmellose sodium, crospovidone or sodium starch glycolate. Croscarmellose sodium is a particularly preferred disintegrant.

The lubricant to be used in accordance with the present invention may be any lubricant known to a person of ordinary skill in the art. Magnesium stearate is a particularly preferred lubricant.

The pharmaceutical compositions of the present invention display dissolution behavior typical for immediate-release formulations, exhibiting a dissolution rate of at least 85% in 15 minutes when tested in 900 ml SGF pH 1.2, pH 2, acetate buffer pH 4.5 or phosphate buffer pH 6.8 in a USP apparatus II at 75 rpm in standard vessels or 50 rpm with peak vessels.

During preparation and storage of the pharmaceutical compositions of the present invention, lenalidomide, or a pharmaceutically acceptable salt thereof, remains in the amorphous form.

The present invention further provides an inclusion complex of lenalidomide, or a pharmaceutically acceptable salt thereof, with a non-substituted β-cyclodextrin, wherein the weight ratio of lenalidomide to non-substituted β-cyclodextrin ranges from 1:1 to 1:4.

The methods and equipment to carry out the process to form the inclusion complex of the present invention are well known in the art.

One possible method is dissolving lenalidomide, or a pharmaceutically acceptable salt thereof, in a suitable solvent or solvent mixture, adding the non-substituted β-cyclodextrin followed by evaporation of the solvent(s). The non-substituted β-cyclodextrin can be suspended or dissolved. Examples of equipments to carry out this evaporation method are fluid bed, high shear mixed and spray drying. Spray dryer is preferred because promotes a rapid evaporation of the solvent. The rapid evaporation of the solvent prevents crystallization. When the fluid bed technology is used additionally a pharmaceutical carrier is needed. Lactose, cellulose, starch and phosphates are the preferred pharmaceutical carriers. Pregelatinized starch, MCC and calcium phosphate are the most preferred pharmaceutical carriers. Even most preferred is calcium phosphate, which gives particularly good results.

The non-substituted β-cyclodextrin exhibit a lower solubility compared to the various semi-synthetic derivatives like 2-hydroxypropyl-β-cyclodextrin, however it is not necessary to dissolve the non-substituted β-cyclodextrin completely. Typically, the mixture of β-cyclodextrin and solvent(s) is heated. Preferably, the mixture is heated from 40 to 60° C.

In an advantageous variant of the process of the present invention, lenalidomide or a pharmaceutically acceptable salt thereof is dissolved in acidic water or a mixture of acidic water and a polar organic solvent and, the non-substituted β-cyclodextrin is added to this solution. Preferred ratio organic solvent:acidic water is 7:3 w/w. Preferred polar organic solvents are alcohols, particularly ethanol or methanol, ethers, particularly tetrahydrofuran, ketones, particularly acetone and acetonitrile. Preferably, 0.1N aqueous HCl or a mixture of acetone and 0.1N aqueous HCl is used. Preferred ratio of acetone:0.1N aqueous HCl is 7:3 w/w. This ratio gives an optimal impurity profile. Advantageously, the inclusion complex is prepared by dissolving lenalidomide in acidic water and acetone by heating, followed by the addition of non-substituted β-cyclodextrin and subsequent evaporation of the solvent.

The inclusion complex can also be prepared by grinding lenalidomide, or a pharmaceutically acceptable salt thereof, with non-substituted β-cyclodextrin, for example using a ball mill. This process to prepare the adsorbate can be carried out without the use of solvents. This process is economically preferred and more environmentally friendly.

The present invention still further provides a process to prepare pharmaceutical compositions comprising an inclusion complex of lenalidomide, or a pharmaceutically acceptable salt thereof, in non-substituted β-cyclodextrin and one or more pharmaceutically acceptable excipients, wherein the weight ratio of lenalidomide to non-substituted β-cyclodextrin ranges from 1:1 to 1:4.

The process comprises mixing or granulating the inclusion complex with one or more pharmaceutically acceptable excipients, followed by encapsulation, using equipment and methods well-known to the skilled artisan. In an advantageous variant of the process of the present invention, a solution of lenalidomide, or a pharmaceutically acceptable salt thereof, and the non-substituted β-cyclodextrin was sprayed over the pharmaceutical carrier e.g. the diluent, in a fluidized bed and the resulting granulate/blend was mixed with one or more pharmaceutically acceptable extragranular excipients, followed by encapsulation. Preferably, a solution of lenalidomide and non-substituted β-cyclodextrin in acidic water/acetone was sprayed over calcium phosphate in a fluidized bed, after which the granulate/powder blend was mixed with microcrystalline cellulose, croscarmellose sodium and magnesium stearate, followed by encapsulation. Preferably, HPMC or gelatin capsules are used.

The pharmaceutical compositions of the present invention are packaged in blister pack material. The blister pack materials to be used in accordance with the present invention may be any blister pack material known to a person of ordinary skill in the art. Suitable blister pack materials to be used in accordance with the present invention are selected from the group of ACLAR® (thermoformable film by Honeywell International, Inc., N.J., USA), PVC/Alu, Duplex/Alu, Triplex/Alu and Alu/Alu. To ensure protection of the compositions of the present invention from e.g. moisture and thereby preventing polymorphic conversions, ACLAR®, Triplex/Alu, and Alu/Alu are particularly preferred blister pack materials. After storage of the pharmaceutical compositions in these blister pack materials for 12 months at 25° C./60% RH, XRPD analysis showed no reflections in accordance with crystalline lenalidomide.

The pharmaceutical composition in accordance with the present invention may be used as a medicament. The pharmaceutical composition typically may be used in the treatment of multiple myeloma and myelodysplastic syndromes.

The following examples are intended to illustrate the scope of the present invention but not to limit it thereto.

EXAMPLES

Example 1, Lenalidomide:β-Cyclodextrin (Weight Ratio 1:2)

The stabilized complex of LNL with cyclodextrin typically has a ratio of API:cyclodextrin=1:2 w/w.

(1) Dissolution: 4 grams of lenalidomide are first added and dissolved in 175 mL of acetone:0.1N HCl (7:3 w/w) solution under heating (50° C.) and stirring conditions. Once the lenalidomide is completely dissolved sequentially 8 g of β-cyclodextrin are incorporated into the dissolution.

(2) Spraying: the (1) resulting dissolution is sprayed into spray drier equipment and the inclusion complex formed is then collected.

(3) Total mixture: the amounts of the following excipients are adjusted base on the complexation process yield obtained in the previous step: 31.95 g of anhydrous lactose, 4.07 g of microcrystalline cellulose and 1.35 g of sodium croscarmellose are mixed with the (2) resulting complex. 0.45 g of magnesium stearate are sieved through a 0.5 mm mesh and mixed with the previous blend.

(5) Capsules: the (4) final blend is then encapsulated into size 0 capsules.

Composition

| | |
|---|---|
| Lenalidomide | 2.39 g |
| β-cyclodextrin | 4.79 g |
| Anhydrous lactose | 31.95 g |
| Microcrystalline cellulose | 4.07 g |
| Sodium Croscarmellose | 1.35 g |
| Magnesium stearate | 0.45 g |

Gelatine capsules size 0

The XRPD pattern of the isolated inclusion complex does not show any reflections in accordance with crystalline lenalidomide.

Example 2, Lenalidomide:β-Cyclodextrin (Weight Ratio 1:2)

(1) Dissolution: 44.44 grams of lenalidomide are first added and dissolved in 1800 mL of acetone:0.1N HCl (7:3 w/w) solution under heating (50° C.) and stirring conditions. Once the lenalidomide is completely dissolved sequentially 88.88 g of β-cyclodextrin are incorporated into the dissolution.

(2) Spraying: the (1) resulting dissolution is sprayed into fluid bed equipment over 568 grams of anhydrous lactose and the resulting blend was dried.

(3) Sieving: the (2) resulting blend is sieved through a 0.71 mm mesh.

(3) Total mixture: 66.64 g of microcrystalline cellulose and 24 g of sodium croscarmellose are mixed with the (2) resulting blend. 8 g of magnesium stearate are sieved through a 0.5 mm mesh and mixed with the previous blend.

(5) Capsules: the (4) final blend is then encapsulated into size 0 capsules.

Composition

| | |
|---|---|
| Lenalidomide | 44.44 g |
| β-cyclodextrin | 88.88 g |
| Anhydrous lactose | 568 g |
| Microcrystalline cellulose | 66.64 g |
| Sodium Croscarmellose | 24 g |
| Magnesium stearate | 8 g |

Gelatine capsules size 0

The XRPD pattern of the isolated inclusion complex does not show any reflections in accordance with crystalline lenalidomide.

Example 3, Lenalidomide: β-Cyclodextrin (Weight Ratio 1:5)

A method for lenalidomide capsules containing the following components was prepared as follows:

(1) Dissolution: 44.4 g of lenalidomide are first added in an acetone:0.1N HCl (70:30) solution under heating (50° C.) and stirring conditions; once the lenalidomide is completely dissolved, sequentially 222.2 g of β-CD are incorporated into the dissolution.

(2) Spraying: the (1) resulting solution is then sprayed into fluid bed equipment over 501.28 g of anhydrous lactose as a carrier.

(3) Sieving: the (2) resulting blend is then sieved through a 0.71 mm mesh;

(4) Total mixture: 24 g of sodium croscarmellose are mixed with the (3) resulting blend. 8 g of sodium stearate are sieved through a 0.5 mm mesh and mixed with the previous blend.

(5) Capsules: the (4) final blend is then encapsulated into size 0 capsules.

Composition

| | |
|---|---|
| Lenalidomide | 44.44 g |
| β-CD | 222.24 g |
| Anhydrous lactose | 501.28 g |
| Sodium Croscarmellose | 24 g |
| Magnesium stearate | 8 g |

Gelatine capsules size 0

The XRPD pattern of the isolated inclusion complex shows crystalline lenalidomide.

Example 4, Lenalidomide:β-Cyclodextrin (Weight Ratio 1:1, 1:2)

The stabilized complex of LNL and cyclodextrin has a ratio of API:cyclodextrin=1:1, 1:2 w/w.

1 part of LNL is mixed together with 1 or 2 parts of β-cyclodextrin. The mixture is homogenized and subsequently ball-milled at 25 osc/sec for at least one hour.

The XRPD pattern of the isolated inclusion complex does not show any reflections in accordance with crystalline lenalidomide.

Example 5, Lenalidomide:Hydroxypropyl β-Cyclodextrin (Weight Ratio 1:1)

A method for lenalidomide capsules containing the following components was prepared as follows:

(1) Dissolution: 8.75 g of HP-β-cyclodextrin are first added and dissolved in an acetone:0.1N HCl (70:30) solution under heating (50° C.) and stirring conditions; sequentially 8.75 g of lenalidomide are incorporated into the dissolution.

(2) Spraying: Once the components of the (1) resulting dissolution are completely dissolved, then the solution is sprayed into fluid bed equipment over 124.25 g of anhydrous lactose as a carrier.

The XRPD pattern of the isolated inclusion complex shows crystalline lenalidomide.

The invention claimed is:

1. A pharmaceutical composition comprising (i) an inclusion complex of amorphous lenalidomide, or a pharmaceutically acceptable salt thereof, with a non-substituted β-cyclodextrin in a weight ratio of lenalidomide to non-substituted β-cyclodextrin ranging from 1:1 to 1:4 and (ii) one or more pharmaceutically acceptable excipients, wherein said composition exhibits a dissolution rate of at least 85% in 15 minutes when tested in at least one of 900 ml SGF pH 1.2 or pH 2, acetate buffer pH 4.5, or phosphate buffer pH 6.8 in a USP apparatus II at 75 rpm in standard vessels or at 50 rpm with peak vessels.

2. The composition according to claim 1, wherein the weight ratio of lenalidomide, or a pharmaceutically acceptable salt thereof, to non-substituted β-cyclodextrin ranges from 1:1 to 1:2.

3. The composition according to claim 1, wherein the pharmaceutical composition is filled in a capsule and the pharmaceutically acceptable excipients are one or more binders, diluents, disintegrants, glidants, lubricants, stabilizers, surface active agents or pH-adjusting agents.

4. The composition according to claim 1 packed in Triplex/Alu or Alu/Alu blister pack material.

5. A process for preparing the pharmaceutical composition according to claim 1, which comprises dissolving lenalidomide, or a pharmaceutically acceptable salt thereof, in a suitable solvent or solvent mixture and mixing with non-substituted β-cyclodextrin, followed by evaporation of the solvent(s) to form the inclusion complex; and
  mixing or granulating the inclusion complex with one or more pharmaceutically acceptable excipients to form said composition.

6. The process according to claim 5, wherein the solvent is acidic aqueous solution.

7. The process according to claim 6, wherein the solvent further comprising acetone.

8. The process according to claim 7, wherein the ratio of acetone:acidic aqueous solution is 7:3.

9. The process according to claim 5, which is carried out in a spray drier or fluid bed.

10. The process according to claim 9 where a fluid bed is used and calcium phosphate is used as pharmaceutical carrier.

11. The process according to claim 5, further comprising encapsulating said composition.

12. A method of treating multiple myeloma or myelodysplastic syndromes, which comprises administering the composition according to claim 1 to a patient in need thereof.

* * * * *